United States Patent
Seifarth et al.

(10) Patent No.: US 8,933,200 B2
(45) Date of Patent: Jan. 13, 2015

(54) FILTRATION OF A LIQUID COMPRISING A PLANT STRESS PROTEIN

(75) Inventors: Friedrich C. Seifarth, Herrliberg (CH); Julia Lax, Brüggen (DE)

(73) Assignee: Alfa Biogene International B.V. (DE)

( * ) Notice: Subject to any disclaimer, the term of this patent is extended or adjusted under 35 U.S.C. 154(b) by 389 days.

(21) Appl. No.: 13/263,445

(22) PCT Filed: Apr. 9, 2010

(86) PCT No.: PCT/EP2010/054723
§ 371 (c)(1), (2), (4) Date: Dec. 22, 2011

(87) PCT Pub. No.: WO2010/115990
PCT Pub. Date: Oct. 14, 2010

(65) Prior Publication Data
US 2012/0095189 A1 Apr. 19, 2012

(30) Foreign Application Priority Data
Apr. 9, 2009 (EP) .................................. 09157774

(51) Int. Cl.
*C07K 14/00* (2006.01)
*C12N 15/79* (2006.01)
*C07K 14/415* (2006.01)
*C07K 1/34* (2006.01)
*C07K 1/36* (2006.01)

(52) U.S. Cl.
CPC ................ *C07K 14/415* (2013.01); *C07K 1/34* (2013.01); *C07K 1/36* (2013.01)

USPC ................................ 530/375; 514/2; 800/278

(58) Field of Classification Search
None
See application file for complete search history.

(56) References Cited

U.S. PATENT DOCUMENTS

| 3,872,016 A | 3/1975 | Bell |
| 6,615,991 B1 | 9/2003 | Rettenmaier |

FOREIGN PATENT DOCUMENTS

| WO | 2005/049645 A1 | 6/2005 |
| WO | 2009/009876 A1 | 1/2009 |

OTHER PUBLICATIONS

PCT/EP2010/054723 International Search Report, (2010).
Miernyk, et al., "ATPase Activity and Molecular Chaperone Function of the Stress70 Proteins," Plant Physiol. (1996) 110: 419-424.

*Primary Examiner* — Anand Desai
(74) *Attorney, Agent, or Firm* — Banner & Witcoff, Ltd.

(57) ABSTRACT

The invention relates to a method for recovering a stress protein from a plant, comprising: obtaining a liquid comprising the stress protein from the plant; precipitating one or more components other than the stress protein from the liquid; adding a fibrous filter aid and a mineral powder to the liquid; then subjecting the liquid comprising the stress protein, precipitated component(s), the fibrous filter aid and the mineral powder to a first filtration step over a filter, thereby separating the precipitate, fibrous filter aid and mineral powder from the filtrate comprising the stress protein; thereafter subjecting the filtrate to a further filtration step; and thereafter purifying the stress protein.

15 Claims, 2 Drawing Sheets

FILTRATION OF A LIQUID COMPRISING A PLANT STRESS PROTEIN

RELATED APPLICATION DATA

Figure 1:
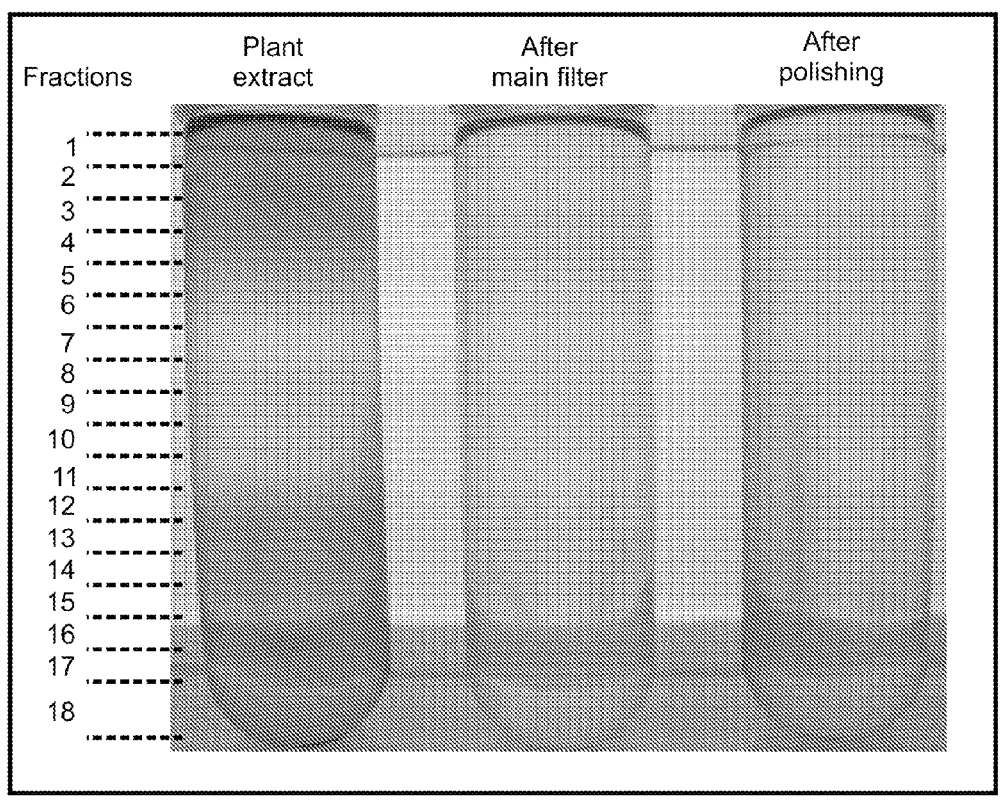

This application is a National Stage Application under 35 U.S.C. 371 of co-pending PCT application number PCT/EP2010/054723 designating the United States and filed Apr. 9, 2010; which claims the benefit of EP application number 09157774.2 and filed Apr. 9, 2009, both of which are hereby incorporated by reference in their entireties.

The invention relates to a method for recovering a stress protein from a plant.

Stress proteins (also called chaperone proteins) are formed by micro-organisms, plants and animals especially when, as a result of a change in the environment such as exposure to heat, radiation or chemicals, so-called stress-susceptible genes are expressed. According to current insights, such proteins can contribute to a protection against detrimental effects resulting from such environmental changes. For that reason, the use of stress proteins is in the centre of interest of, inter alia, medicine, molecular biology, the cosmetic industry and the industry producing plant protection products.

It is known that stress proteins have a number of important natural therapeutic functions in plants and animals, people included. These proteins are involved as regulator in protein synthesis and protein folding. In addition, an important function lies in the regulation of gene function during growth, but also during cell death. The stress proteins are capable of stimulating both human and animal immune systems, and clinical research has shown that the chaperone proteins contribute positively in the fight against cancer.

However, the availability of stress proteins such as HSP70 and other heat shock proteins is a problem as they are often isolated from bovine brain. In addition to the slight amounts that can be isolated there from and the accompanying extreme high cost price, the possible presence of BSE in brain is a large impediment to the use of these proteins. HSP70 can also be produced from micro-organisms and cancer cells, but these production methods too are expensive and only give a low yield.

Alternatives to the production of the stress proteins, in particular for medical uses, lie in the field of the production of fusion proteins with the aid of expression systems. Possible problems that may continue to exist are the high cost price and the small amounts that can be produced.

Stress proteins of vegetable origin could offer an alternative. As the production of stress proteins depends on the condition the cell is in, a change in the circumstances outside the cell can tremendously increase the synthesis of the stress proteins in the plant cell.

WO 2005/049645 describes a method for recovering a heat shock protein, comprising subjecting a fluid comprising the heat shock protein to a) precipitation; thereafter to b) at least one ion exchange separation; and thereafter to c) at least one affinity separation. Although such method is suitable to obtain heat shock proteins with a high degree of purity and activity, problems may be encountered with respect to blocking of the process line after the precipitation, in particular when the process is carried out at an industrial scale.

The inventors have evaluated several separation techniques for the precipitate, such as centrifugation or a conventional filtering technique have been found to be problematic, especially when employed at an industrial scale.

In particular problems have been observed with respect to blocking during further purification of the protein, especially in a stress protein concentration unit (e.g. an ultrafiltration unit), dialysis unit and/or chromatography unit downstream of the precipitate. It is the inventors finding that such problem especially occurs when recovering the stress protein from leaves.

Further, separation based on centrifugal forces (using a disc separator (SC6-06-576, Westfalia), 12000 rpm) was found to be insatisfactory. It is contemplated that the required g-force to effectuate separation is higher than achievable with the disc separator that was used, to make this technique practical on an industrial scale. When decantation was used, considerable foaming of the underflow comprising the HSP was observed, which foaming is undesired because it can easily cause overflows of foam (with product loss) and due to intimate contact with air the stress protein tends to suffer from oxidation.

It is an object of the invention to provide a novel method for recovering a stress protein, in particular a method that can satisfactorily be employed at an industrial scale.

It is a further object of the invention to provide a novel method with reduced tendency to blocking of equipment used in a purification step of the stress protein.

It is a further object of the invention to provide a novel method which allows the recovery of a stress protein from a liquid, in particular a plant juice, with a high yield and satisfactory purity.

One or more other objects that may be solved in accordance with the invention are apparent from the present description and/or claims.

It has now been found possible to meet one or more of said objects by adding specific aids to the liquid comprising stress protein, obtained from a plant.

Accordingly, the present invention relates to a method for recovering a stress protein from a plant, comprising subjecting a liquid comprising stress protein, obtained from a plant to filtration, wherein for the filtration is use is made of a fibrous filter aid and a mineral powder.

In particular, the present invention relates to a method for recovering a stress protein from a plant, comprising
a) obtaining a liquid comprising the stress protein from the plant;
b) precipitating one or more components other than the stress protein from the liquid;
c) adding a fibrous filter aid and a mineral powder to the liquid; then
d) subjecting the liquid comprising the stress protein, precipitated component(s), the fibrous filter aid and the mineral powder to a first filtration step, thereby separating the precipitated component(s), fibrous filter aid and mineral powder from the filtrate comprising the stress protein; thereafter
e) subjecting the filtrate from filtration (d) to a second filtration step, in particular a polishing step; and further
f) purifying the stress protein.

The invention further relates to the use of at least one mineral powder selected from the group of diatomaceous earth and perlite to remove at least one compound selected from the group of chlorophyll, carotenoids and lipids from a liquid, in particular a plant juice, containing a stress protein, in particular a heat shock protein. In a specific embodiment, the mineral powder is used in combination with organic fibrous particles.

In accordance with the invention, it has been found possible to increase the throughput of fluid from which stress protein is to be isolated compared to a method according to WO 2005/049645 (employed on a comparable scale), whilst a satisfactory purity and stress protein activity is maintained. At least in some embodiments, a method according to the invention results in improved yield of stress protein.

Further, it has been found that a method according to the invention can be operated for a long time, without unacceptable blocking in the filtration step or another step of the method.

In particular, it has been found that the fraction comprising stress protein (enriched in stress protein, compared to the liquid prior to the first filtration) after the second and further filtration step has a high optical clarity. In particular it has been found possible that the filtration is very suitable to rubisco, chlorophyll and/or proteolytic enzymes.

A method according to the invention is in particular suitable to recover a heat shock protein of a plant, more in particular one or more heat shock proteins selected from the group of HSP40, HSP60, HSP70 and HSP90.

The term "or" as used herein is defined as "and/or" unless specified otherwise.

The term "a" or "an" as used herein is defined as "at least one" unless specified otherwise.

When referring to a moiety (e.g. a compound) in the singular, the plural is meant to be included, unless specified otherwise.

As referred to herein, bulk compounds are compounds that are contained in a large amount (compared to the stress protein) in the liquid from which the desired stress protein can be produced, such as proteins and other peptidic compounds and other contaminants that are not stress proteins. Typical examples of bulk compounds are chlorophyll and proteins such as complexes of chlorophyll with "chlorophyll binding proteins", rubisco, enzymes (for instance proteases, phosphatases and polyphenol oxidases) and other proteins present in the liquid to such a degree that they impede efficient production of the stress protein. Inconvenient proteins, such as rubisco, "chlorophyll binding protein" and chlorophyll protein complexes are referred to herein as bulk proteins. Further, the term 'bulk compounds' includes plant cell remains, such as cell wall remains and DNA.

The liquid may in particular from at least one part of the plant selected from leaves, stems, roots and flowers. Before obtaining the liquid from the plant material the (harvested) plant material may be treated by a HSP inducing treatment. Examples of such treatments are known in the art, e.g. from WO 00/70931 or WO 02/98910. A heat treatment may be carried out by subjecting harvested plant material to a temperature in the range of 20 to 60° C., preferably 30 to 50° C. more preferably 35 to 45° C. The duration may be chosen in a wide range, e.g. from 0.1-100 hours, preferably 1-12 hours.

The liquid may be obtained in a manner known per se, e.g. by squeezing/pressing or by liquid-extraction. Suitable preparation methods for such a liquid are known, for instance from WO 00/70931 and S. Lewis et al, Ecotoxicology 8, 351-368 (1999). Extraction can for instance take place with water or another solvent in which stress proteins dissolve. From the crude liquid obtained from the plant, cell debris and other relatively large particles may be removed, prior to precipitation. To that purpose sieving is in particular suitable (e.g. using a sieve with a mesh size of 20 µm or more).

Preferably the stress protein is obtained from a plant selected from the group of Fabaceae, Chenopodiaceae, Solanaceae and Poaceae, in particular from the group of alfalfa (lucerne), wheat, maize, rice, soy, beet, barley, oat, more in particular from the group of alfalfa, clover, oat and barley. In particular good results have been achieved with a liquid (plant juice) obtained from alfalfa, especially from the leaves and/or stems thereof.

The plant material used for obtaining the liquid may have been treated after harvesting by a HSP inducing treatment. Examples of such treatments are known in the art, e.g. from WO 00/70931 or WO 02/98910.

The liquid comprising the stress protein that is obtained from the plant will usually be an aqueous liquid. Although one or more other liquid substances, in particular one or more other polar liquid substances (e.g. glycerol (which is a liquid above 18° C.), mercapto-ethanol, isopropanol, see below) may be added to the liquid prior to the filtration, water will usually be the major solvent in the liquid that is subjected to filtration. In particular, the water content of the liquid that is filtered may be 60-100 wt. %, based on total liquid substances, more in particular 80-100 wt. %, based on total liquid substances, even more in particular 95-100 wt. % based on total liquid substance. A liquid substance, as used herein is compound that has a melting point below the filtration temperature and a boiling point above the filtration temperature, for instance a substance with a melting point below 20° C., or below 4° C. at 1 atmosphere and a boiling point above 40° C.

The pH of the liquid subjected to filtration, as measured at 25° C. with a pH meter (pH 3301 WTW) is usually in the range of pH 5-9, in particular in the range of 6-9; the pH of the liquid may be brought in said range by adding an acid or base. To the liquid one or more additives may be added, in particular at least one additive selected from buffers (preferably buffering the solvent at an alkaline pH) protease inhibitors such as phenylmethylsulfonylfluorid (PMSF), Pefabloc SC, leupeptide, pepstatin, protein stabilizers such as mono- and divalent metal ions (e.g. $Na^+$, $K^+$, $Mg^{2+}$, $Ca^{2+}$, $Mn^{2+}$), antioxidants such as ascorbate, dithiothreitol, dithioerythritol, β-mercaptoethanol, sodium dithionite, sodium diethyldithiocarbamate etc. and anti-denaturants such as glycerol, mono-, di-, and oligosaccharides (e.g. glucose, sucrose, trehalose), sugar alcohols (e.g. sorbitol, inositol), ethylenglycol and polyethyleneglycol (in particular having a molecular weight in the range of 2 to 40 kDa), chelating agents such as EDTA and EGTA and the like.

The skilled person will know how to choose suitable concentrations and combinations of said additives, based upon common general knowledge and the information disclosed herein.

As a guidance, typical concentrations for protease inhibitors may be about 0.05 µg/ml to about 1 mg/ml, for divalent metal ions about 0.1 to about 10 mM, for antioxidants about 0.1 to about 30 mM, anti-denaturants about 5 to about 30% (w/v), and for the chelating agents about 0.1 to about 50 mM.

The precipitation (b) may be carried out in a manner known per se, e.g. from WO 2005/049645. The stress protein fraction usually is the supernatant of at least one precipitation step; the precipitate usually comprises one or more other biopolymers, such as other proteins, and/or bulk components, such as cell wall remains, etc.

The supernatant comprising stress protein may be subjected to the filtration or may be subjected to a further precipitation step. Such a precipitation process is called differential precipitation.

The term differential precipitation is used herein to describe a precipitation procedure, wherein first components other than stress protein are preferentially precipitated and preferably removed from the supernatant (comprising stress protein) in at least one precipitation step. The differential precipitation is in practice carried out by gradually or stepwise increasing the saturation degree or concentration of a precipitation agent. The saturation degree may be increased by adding precipitation agent, by changing the temperature, by addition of another solvent or a combination thereof.

Usually, the supernatant comprising stress protein is subjected to the filtration without further precipitation, although in principle it is possible to precipitate the stress protein. In an embodiment wherein the stress protein is precipitated, it is normally resuspended in liquid and then subjected to filtration (after the filter aids have been added to the liquid).

The temperature during precipitation and the rest of the purification process may be ambient (e.g. about 25° C. or less). For practical reasons, the temperature is preferably below about 10° C., more preferably between about 0 and about 4° C.

Suitable precipitation agents include inorganic salts—in particular ammonium sulphate, sodium chloride, and other halogenides, sulphates and phosphates of alkali metals and ammonia, organic salts, such as acetates and citrates of alkali metals, and organic solvents such as acetone, acetonitrile, and alcohols (in particular methanol, ethanol, isopropanol).

The precipitation may be carried out with one precipitation agent or with several. For instance in a first step (which may be the only step) a relatively mild agent (e.g. NaCl) may be used at a saturation degree or concentration at which the stress protein remains substantially dissolved. It is also possible to use a relatively strong precipitation agent (e.g. ammonium sulphate) at a concentration at which the stress protein remains substantially dissolved. precipitation wherein an impurity is precipitated in one or more steps by using a precipitation agent, preferably ammonium sulphate, in a relatively low saturation degree (sufficiently low to maintain the majority of stress protein in solution), in particular at a saturation degree in the range of about 10 to about 40%, more in particular in the range of about 30 to about 40% saturation, removing the precipitate from the supernatant.

The liquid comprising the stress protein may thereafter advantageously be subjected to the filtration (after addition of filter aids) without further precipitation step. The precipitated particles do not need to be separated from the liquid prior to the filtration (d).

Filtration (d) is in general a depth filtration. Filtration (d) may herein after also be referred to as a primary filtration. Depth filtration has been generally known in the art for decades, see e.g. Ullmans Encyclopädie der technischen Chemie (Verlag Chemie, Weinheim), see e.g. $4^{th}$ edition, Volume 2, the Chapter "Filtration starting at page 154, in particular §2.3. With depth filtration particles are removed from the liquid within the depth structure of the filter medium itself. In particular, the particles may either be mechanically trapped in the pores of the filter medium or absorbed on the internal surface of the pores of the filtration medium.

In general, the filter medium is formed of at least a support material through which the liquid can pass and the filter aids (the fibrous filter aid and the mineral powder), which typically form a filter cake or precoat layer, which is supported by the support material. The support material itself may also have filtering properties, or may be inert with respect to the filtration. Suitable support materials are generally known in the art. For instance the depth support material can be made of paper, fabric or bonded filter aids, or be a metallic or plastic woven screen. The size of the openings in the support material should be fine enough to retain substantially retain the filter aid particles, especially the fibrous filter aid, and allow a firm cake to be formed quickly while at the same time giving a low resistance to flow. Suitably, a support material having pores in the range of 1-50 μm may be used. In particular, the pore size may be at least 5 μm, more in particular 10 μm or more or 15 μm or more. In particular, the pore size may be 30 μm or less, more in particular at least 25 μm or less or 20 μm or less.

The fibrous filter aid and the mineral powder are generally added to the liquid after precipitation step (b). Thereafter the liquid is subjected to filtration (d).

The filter aids form a porous layer (filter cake) on the support material wherein solids from the liquid are trapped. Herewith, unacceptable blocking of the support material is avoided.

The primary filtration (d) is in particular suitable to remove the bulk of plant cell wall remains, precipitated proteins (other than the stress protein) and other not wanted parts of the cells (specially chlorophyll). It has been found that if the filtrate of this filtration step is not subjected to a further filtration step, problems with respect to throughput and/or product loss may occur further downstream of the method. In particular problems may occur during purification, e.g. during dialysis and/or chromatography. It is contemplated that in particular some filter aid may pass through the primary filter, especially if the support material in the primary filtration step has relatively large openings relative to the average particle size of one or more of the filter aids. Using a support material with smaller openings is in principle an option, but will result in an increased pressure requirement to pass the liquid though, a higher risk of blocking, and/or may lead to reduced product yield.

Optionally, to the filtrate of filtration step (d) fibrous filter aid and/or mineral powder may be added after which a filtration step (d) is repeated at least once. This may in particular be desired in case the chlorophyll and/or carotenoid concentration in the liquid obtained from the plant are high.

After the (final) filtration step (d), a secondary filtration step (e) is performed. This step (e) is generally carried out without adding mineral powder. Addition of fibrous filter aid is generally not required either. The filtrate of the first filtration may be subjected to one or more intermediate treatment steps, but good results have been achieved without such intermediate steps, which is advantageous for reasons of providing a relatively simple process. Further, omitting intermediate steps may offer benefit in that the stress protein yield is improved. For instance, secondary filtration is advantageously carried out without first subjecting the filtrate of the primary filtration to a centrifugation step.

Secondary filtration (e) in particular suitable to remove filter aid that is present in the filtrate of the (final) primary filtration step (d). Also, secondary filtration may be useful to remove one or more components originating from the plant that have not been removed during primary filtration, whereby this step may also be an effective part in the purification of the stress protein. Further, it has been found that after primary filtration, the filtrate may still comprise undesired impurities, such as carotenoids and/or lipids. Without being bound by theory, it is contemplated that in particular if the pore size of the support material in the primary filtration is such that a (minor) part of the mineral powder is allowed to pass through this material, this part of the mineral powder may then further contribute to removal of undesired compounds that hayed pass through the primary filter in the filtrate, together with the stress protein.

The addition of additional mineral powder and fibrous filter aid to the filtrate of the primary filtration is usually omitted. Such a secondary filtration wherein no filter aids are added to the liquid that is to be filtrated (i.e. to the filtrate obtained from the primary filtration) may also be referred to as a polishing step. For the secondary filtration a porous (e.g. fibrous woven or non-woven) filter (e.g. a filter sheet or membrane) can be used, e.g. a material as described above for the support material. In general, the openings in the filter for the secondary filtration, are smaller than in the primary filtration step. Usually, the filter is chosen such that the openings are 1 μm or less. A pore size of up to 0.45 μm is in particular preferred as this is in general sufficient to remove components that may cause blockage problems during further purification, e.g. ultrafiltration, dialysis and/or chromatography.

Alternatively, such components may be removed by a separate filtration, e.g. by passing the filtrate of the secondary filtration through a separate filter, such as a standard 0.45 µm or 0.2 µm solid filter medium, as a are commercially available.

The lower limit of the pore size of the filter of the secondary filter is determined by the minimum pore size that allows the stress protein of interest to pass. For stress protein having a molecular weight of 70 g/mol or more, the pore size usually should be more than 0.1 µm, in particular a support material with a pore size of at least 0.2 µm may be used. After the secondary filtration step (e), in general a transparent filtrate comprising stress protein is obtained. Compared to the filtrate of the primary filtration, and in particular compared to crude liquid obtained from plant material (by pressing), such secondary filtrate in particular can be characterized by a low extinction coefficient at 440 nm and at 676 nm (light absorption maxima of chlorophyll), and/or at 330 nm (light absorption maximum of carotenoid), and/or at 260 nm (light absorption maximum of DNA) as measured by UV/VIS Spectroscopy, relative to the extinction at 280 nm (characteristic for protein).

The inventors have come to the conclusion that it is important to use both a fibrous filter aid and a mineral powder in combination for efficient removal of unwanted components, in particular chlorophyll.

A filter sheet, support material for the filter aid, fibrous filter aid or mineral powder used in a method according to the filter are preferably is hydrophilic in nature. Hydrophilic filter aids and hydrophilic filter sheets are wettable by water, in particular better wettable with water than with an apolar liquid (e.g. hexane or another hydrocarbon). The skilled person will be able to determine whether a filter sheet, fibrous filter or mineral powder is hydrophilic, and thus wettable with water, for instance by determining the contact angle of a droplet of water on a surface made from the same material filter sheet, fibrous filter aid or mineral powder, based on common general knowledge and/or information provided by the supplier. In particular, the contact angle θ between a droplet of water and the material (provided as a flat surface) of a water-wettable material is 0-90° It should be noted that it has been described in the art to provide modified filter aids of which the surface has been made hydrophobic, e.g. with a surfactant. As will be understood by the skilled person, such modified materials are not hydrophilic filter aids.

The weight percentage fibrous filter aid, based on the sum of the total fibrous filter aid weight and the total mineral powder weight may be chosen within wide limits, generally within the range of 25 to 95 wt. %. Preferably, said weight percentage fibrous filter aid is at least 40 wt. %, in particular at least 65 wt. %, more in particular at least 70 wt. %. Preferably, said weight percentage fibrous filter aid is 90 wt. % or less, in particular 85 wt. % or less, more in particular 80 wt. % or less. A relatively low percentage of fibrous filter aid—and thus a relatively high percentage of mineral powder—may in particular be advantageous for effectively removing chlorophyll, also if the chlorophyll is relatively high. A relatively high percentage of fibrous filter aid—and thus a relatively low percentage of mineral powder—may in particular be advantageous for a high product yield.

The mineral powder may be a mineral powder known per se. Such filters aids have been known for use in filtration technology for decades, for instance as described in Ullmans Encyclopädie der technischen Chemie (Verlag Chemie, Weinheim), see e.g. 4$^{th}$ edition, Volume 2, in particular pages 195-198. In particular, at least one mineral powder selected from the group of porous mineral powders may be used. The permeability of such powder may be chosen within a wide range, in particular in the range of 0.02-0.26 Darcy. In particular, good results have been achieved with a porous mineral powder having a relatively low permeability for water, in particular a permeability in the range of 0.03-0.1 Darcy. In accordance with the invention, the mineral powder is advantageously used without having been surface-modified, to make the surface more hydrophobic.

Preferred mineral powders are diatomaceous earth and perlite. Diatomaceous earth is for instance commercially available under the trademark Becogur® (from Begerow, Germany). Further examples of mineral powders are clay powders such as bentonite.

The fibrous filter aid may be a fibrous filter aid known per se. For instance fibrillic cellulosic filter aids, cotton linter, or another fibrous organic material may be used may be used, Such filters aids have been known for use in filtration technology for decades, see e.g. Ullmans Encyclopädie der technischen Chemie (Verlag Chemie, Weinheim), see e.g. 4$^{th}$ edition, Volume 2, pages 195-198. Further examples are provided in U.S. Pat. No. 6,615,991. Filter aid types used in solid-liquid separations include: inorganic mineral powders, which comprises processed diatomaceous earth, known as diatomite; perlite, a vitreous aluminium silicate of volcanic origin; and organic fibrous materials such as cellulose and cotton linter. In accordance with the invention, the fibrous filter aid is advantageously used without having been surface-modified, to make the surface more hydrophobic.

For an advantageous removal of unwanted components preferred method, the fibrous filter aid is a mixture of fibres having a different length, the mixture at least providing fibres with a length over the range of about 20 µm to about 130µ. Preferably, the majority (at least 50 wt. %) of the fibrous filter aid is formed by such fibres, more preferably 75-100 wt. %, in particular 95-100 wt. %. The balance is preferably at least substantially formed by fibres having a length of 1-500 µm. In particular, good results have been achieved with a fibrous filter aid (mixture) comprising, a first fibrous filter aid fraction consisting of relatively small fibres (20-40 µm) and a second fibrous filter aid fraction consisting of large fibres (80-130 µm). Further such filter aid (mixture) preferably comprises a further fibrous filter aid fraction consisting of fibres of intermediate length (between 40 and 80µ). In such embodiment, the large fibres may make up in particular 33-80 wt. % of the fibrous filter aid, more in particular 40-60 wt. %. In such embodiment, the small fibres may make up in particular 10-50 wt. % of the fibrous filter aid, more in particular 20-33 wt. %. In such embodiment, the intermediate fibres may make up in particular 10-50 wt. % of the fibrous filter aid, more in particular 20-33 wt. %.

By carefully selecting the type and grade as well as quantity of the added filter aids through put through the filter and clarification (reducing turbidity) is improved.

Filter aid dosage varies with the solids content and other variables specific to each application. Usually, the amount of filter aid (fibrous filter aid plus mineral powder taken together) added to a liquid prior to a depth filtration in accordance with the invention is at least 2 wt. % based on the total weight of the liquid to be filtered, in particular at least 3.5 wt. %, more in particular at least 4.5 wt. %. Usually, the amount is 8 wt. % or less, in particular 6.5 wt. % or less, more in particular 6.0 wt. % or less. In an advantageous embodiment, the amount of added filter aid is at least about half the amount of precipitate in the liquid to be filtered. In an advantageous embodiment, the amount of added filter aid is about the same as the amount of precipitate in the liquid to be filtered, or less.

In a specific embodiment, the pH of the fibrous filter aid and/or of the mineral powder (measured at 25 C, 1 wt. % dispersion in water) is in the range of 5-8, in particular in the range of 6-7.5. This is considered advantageous with respect to avoiding adverse reaction, such as hydrolysis, of the stress protein at the surface of the filter aid.

After (depth) filtrations (d, e), the filtrate is subjected to a purification process, wherein stress protein is purified.

In an embodiment, the filtrate (comprising stress protein) is subjected to a water removal step thereby concentrating the stress protein in the fraction. Water removal is preferably carried out by dialysis, reversed osmosis or a further filtration such as cross-flow filtration, which may be a nanofiltration or an ultrafiltration.

In a further embodiment, which may be combined with the water removal step or carried out thereafter or before, the liquid comprising stress protein is subjected to a salt removal step, preferably by dialysis.

The purification of stress protein, in particular of a heat shock protein, may in particular comprise one or more separations by chromatography. Suitable methodology may be based on known technology, for instance as described in WO 2005/049645, of which the contents with respect to the description of suitable chromatography is incorporated by reference, in particular, the contents of page 13, line 8 to page 20 line 4.

In a preferred method, the purification by chromatography comprises a first strong ion exchange, thereafter an affinity chromatography separation, and thereafter a second strong ion exchange. In a particularly preferred method both of said ion exchange steps are strong anion exchange steps. Such a method is considered particularly advantageous for a high product yield, compared to a method wherein the first ion exchange step is a weak anion exchange step.

Preferred strong-ion exchange materials include beaded pressure resistant gels such as crosslinked agarose, sepharose and silica derivatised with functional groups such as trimethyl ammoniumethyl (TMAE), (e.g. MonoQ™, Resource Q™, TMAE Fractogel™).

Separation conditions for the strong-ion exchange separation (before and/or after affinity separation) may be chosen such as specified in WO 2005/049645 for the weak ion exchange step as described from page 14 line 20 to page 16, line 6, of which the contents are incorporated by reference. The skilled person will know how to choose suitable conditions based upon the information disclosed herein and common general knowledge.

The affinity separation has been found very suitable to remove one or more remaining bulk components, in particular remaining proteins.

An affinity separation is preferably carried out by affinity chromatography (including an affinity chromatography based technique such a solid phase extraction based upon affinity extraction, electrokinetic chromatography and the like).

Preferably, the affinity separation comprises affinity chromatography with a nucleotide coupled to a matrix.

Preferred matrices include agarose, sepharose, polyacrylamide, silica, and cellulose. Very good results have been achieved with agarose as a matrix material.

In principle any type of nucleotide, in particular any nucleotide triphospate (NTP) or nucleotide diphosphate (NDP), may be used for the affinity separation. Very good results have been realised with an adenosine based affinity separation, in particular an ATP or ADP based affinity separation. For further details on the affinity chromatography, reference is made to page 17, line 23 to page 19 line 25 of WO 2005/049645, which is incorporated herein by reference.

In particular, good results have been achieved in a method wherein the median particle size of the exchange material used in the first anion exchange is larger than the median particle size of the exchange material used in the second anion exchange, in particular at least 1.5 larger, more in particular 2.0-5.0 times larger. This is considered to be advantageous to achieve a high degree of purification in combination with a good liquid through-put.

After the separation(s) by affinity and/or ion exchange chromatography, the purified product comprising the stress protein may be directly used or further processed.

A further purification may be carried out, e.g. to remove larger or smaller proteins than the stress protein of specific interest. Suitable size separation procedures are generally known in the art and include size exclusion chromatography, dialysis, and native state electrophoresis.

Further, purified liquid comprising the stress protein may be subjected to a further concentration step (e.g. by nanofiltration, evaporation of liquid).

The stress protein thus obtained (dried or in liquid form) may then be used, e.g., as an ingredient for a pharmaceutical product, a nutritional product or a cosmetic product.

For instance, in an embodiment the stress protein is combined with a pharmaceutically acceptable excipient to provide a pharmaceutical product, which may done in a manner known per se.

In a further embodiment, the stress protein is combined with one or more additional food ingredients in a process for preparing the food in a manner that is otherwise known per se. E.g. it may be combined with one or more other proteins and/or peptides (if present) which combination can then be further processed to product the food product of interest. Depending on the food product, it is also possible to add the stress protein to the food product already comprising the other ingredient(s).

In a further embodiment, the stress protein is combined with one or more additional ingredients for a cosmetic product, such as a for skin care in a manner that is otherwise known per se, e.g. it may be combined with one or more other proteins and/or peptides (if present) which combination can then be further processed to product the skin care product of interest. Depending on the skin care product, it is also possible to add the stress protein to the cosmetic product already comprising the other ingredient(s).

The invention will now be illustrated by the following examples.

EXAMPLE 1

Filtration and Subsequent Purification of HSP

Hsp70 was purified out of *Medicago sativa*. Approximately 250 kg of freshly cut plant was heat induced for 2 hours at 43-45° C. Plant extract was afterwards prepared by pressing in a Ponndorf screw press.

Cell debris and particles greater than 20 µm were removed using a Sweco sieve. Before cooling down the juice in a cooling container, lyse buffer has been added and cooled down before in the ratio of 1 lyse buffer part to 3 parts of raw juice. Composition of lyse buffer was as follows:

| | |
|---|---|
| 150 mM Tris HCL pH 8.0 | (18.2 g/l) |
| 150 mM (NH$_4$)SO$_4$ | (19.8 g/l) |
| 15 mM MgCl$_2$ | (3.1 g/l) |
| 30 mM EDTA | (13.6 g/l) |
| 30% Sucrose | (45 g/l) |
| 42 mM β-Mercaptoethanol | (2.9 g/l) |
| 60 mM Natriumdiethyldithiocarbamat | (13.5 g/l) |
| 50 mM PMSF dissolved in 1 l Isopropanol | (8.71 g/l) |

After cooling down the raw juice to 4° C. the juice was subjected to ammonium sulphate precipitation at 4° C. using 194 g ammonium sulphate per liter crude juice.

After 60 minutes precipitation, filter aids (fibrous filter aid and mineral powder) for the primary depth layer filter step were added in the following amounts (weight % based on total weight of the liquid, including precipitate in the liquid):

Fibrous filter aids: 2% Arbocel B800 (average length 130 μm) 1% Vitacel L60 (average length 60 μm) and 1% Vitacel L20 (average length 23 μm) mixture.

Mineral powder 0.5% Becogur 100 (permeability about 0.04 Darcy).

The depth layer filtering was done with a Begerow Beco-Integra Plate 400 EC with 4, 5 or 6 frames (400×400 mm) and 4, 5 or 6 sheets. As support material (upon which the filter aids are allowed to form a filter cake) depth layer sheets with a poresize of 20 μm from Begerow were used.

The filtrate from this primary filter step was subjected to a secondary filtration, by passing the filtrate through a filter sheet with a poresize of 0.2 μm (Begerow).

The effect of the first (main filtration) and the second filtration (polishing) is illustrated by the following. In order to give a first review, which components of the plant extract are filtrated using the different filter aid components sucrose density gradient centrifugation was used.

For this experiment a sample comprising 20 mg of Protein of each fraction (plant juice, extract after primary filtration and extract after secondary filtration) were added on a 10-30% sucrose density gradient. This was prepared as follows: 20% (w/v) sucrose in buffer (20 mM MES NaOH, pH 6.5, 10 mM CaCl$_2$, 10 mM MgCl$_2$, 0.03% (w/v) β-dodeycl maltoside). was filled into 36 ml ultracentrifuge tubes (polyallomer tubes, 14×89 mm, No. 331372, Beckman). At −20° C. the filled tubes were frozen over night. The defreezing was done at room temperature. This resulted in a linear gradient from 10-30% (w/w) sucrose (Lax, 2005). Samples were added onto the gradient and the gradient was centrifuged for at least 18 hours (Beckman ultracentrifuge, SW28 rotor, 25.000 rpm, 4° C.). The gradients were harvested by inserting a syringe tip at the bottom of the tube and collecting of 2 ml fractions with the help of a peristaltic pump.

As illustrated in FIG. 1, two intense bands were visible in the crude plant juice sample subjected to gradient centrifugation. The upper band (between fractions 1-6) is orange-brown and probably contains carotenoids and lipids. The lower band (from fraction 11 downward) is green and at least contains chlorophyll. The primary filtration is effective in removing most, if not all, of the chlorophyll, but an orange fraction was still visible in the primary filtrate sample subjected to gradient centrifugations (fractions 1-6). The second filtration in particular resulted in a further removal of impurities from these fractions.

Absorption of filtrate after primary filtration and after secondary filtration was also determined using Beckman DU 7400 Diodearray detector for fractions 4, 8 and 16 of the sucrose gradient (as indicated in FIG. 1). The values at wavelengths indicative for DNA (260 nm), protein (280 nm), chlorophyll (440 nm, 676 nm), and carotenoids (330 nm) were as follows:

| | Plant juice | After primary Filter | After secondary filter |
|---|---|---|---|
| Fraction 4 | | | |
| 260 nm | 7.716 | 8.0045 | 2.8068 |
| 280 nm | 7.157 | 7.239 | 2.1638 |
| 440 nm | 0.405 | 0.1025 | 0.0402 |
| 676 nm | 0.016 | 0.0225 | 0.0054 |
| 330 nm | 5.745 | 2.3845 | 0.5328 |
| Fraction 8 | | | |
| 260 nm | 1.8975 | 1.6158 | 0.7811 |
| 280 nm | 1.5375 | 1.4261 | 0.8133 |
| 440 nm | 0.0719 | 0.0261 | 0.02 |
| 676 nm | 0.0259 | 0.0014 | 0.0225 |
| 330 nm | 0.4845 | 0.5064 | 0.472 |
| Fraction 16 | | | |
| 260 nm | 0.3931 | 0.092 | 0.118 |
| 280 nm | 0.3417 | 0.0743 | 0.0953 |
| 440 nm | 0.3307 | 0.0177 | 0.0038 |
| 676 nm | 0.2056 | 0.0195 | 0.0047 |
| 330 nm | 0.2483 | 0.0418 | 0.0172 |

These data and FIG. 1 support that after primary filtration most chlorophyll and most chlorophyll containing proteins are removed (or any other impurity having substantial absorption at the same wavelength) and that secondary filtration is effective in removing residual chlorophyll and also carotenoids (or any other impurity having substantial absorption at the same wavelength).

After secondary filtration, filtrate from the secondary filtration was subjected to ultrafiltration (50 kD MW cut off (Sartocon cassette), different filter may be chosen depending on stress protein that is to be purified) to concentrate to filtrate of the secondary filtration step 10 fold.

The retentate of the ultrafiltration (comprising HSP 70) was subjected to dialysis against a buffer solution (pH 7.8) comprising 10% glycerine and 0.25 M HEPES, 5 mM KCl, 5 mM MgCL$_2$, 9 mM β-Mercaptoethanol, 1 mM EDTA (adjusted to pH 7.8 with KOH), again using a membrande with a 50 kD molecular weight cut off (Sartocon cassette). Salt and sugars were removed. A dialysate comprising HSP 70 was obtained having a conductivity below 5 mS/cm.

Thereafter, the dialysate was subjected to chromatography.

As a first chromatography step strong anion exchange with gradient elution was used with a ion exchange material having a median size of 120 μm (UNOsphere Q support). Buffer A contained 10% glycerine and 0.25 M HEPES, 5 mM KCl, 5 mM MgCL$_2$, 1 mM EDTA (adjusted to pH 7.8 with KOH) and 0.0007 vol % beta-mercaptoethanol. Buffer B was as buffer A but with an additional 75 g/l KCl. After applying the supernatant to the chromatography column, first isocratic flow was applied (A:B 95:5). After 5 column volumes had eluted, gradient elution was initiated starting from a ratio A:B of 95:5 to 5:95 over 2.5 column volumes. Thereafter, the fraction comprising stress protein (HSP 70) was eluted with buffer B.

The eluate comprising HSP 70 was subjected to ATP-affinity chromatography, by adding 5 ml ATP sepharose to 4.5 liters of the eluate. The mixture was incubated for 30 min and thereafter loaded into an empty Econocolumn. This step was repeated twice. After washing with buffer B and buffer A, the HSP 70 was eluted with elution buffer C, which is as buffer A but to which 0.2 mg/ml MgCl$_2$ and 5.5 mg/ml ATP had been added.

The eluate was subjected to another strong anion exchange, this time with Macro-Prep® 25 Q (median bead size 25 μm), using the same buffers A and B as described for the first ion exchange. the gradient was as follows:
First gradient: 0% B to 10% B over 5 column volumes.
Second gradient: 10% B to 30% B over 20 column volumes
HSP was eluted from the column by buffer B during the second gradient. Target protein was concentrated and desalted.

The HSP may be lyophylized after changing the buffer into a buffer which is free of glycerine.

The isolated protein was identified via Western Blot and MALDI-ToF Analysis. The purity, shown on SDS-Gel Electrophoresis was at least about 95%.

Figure 2:
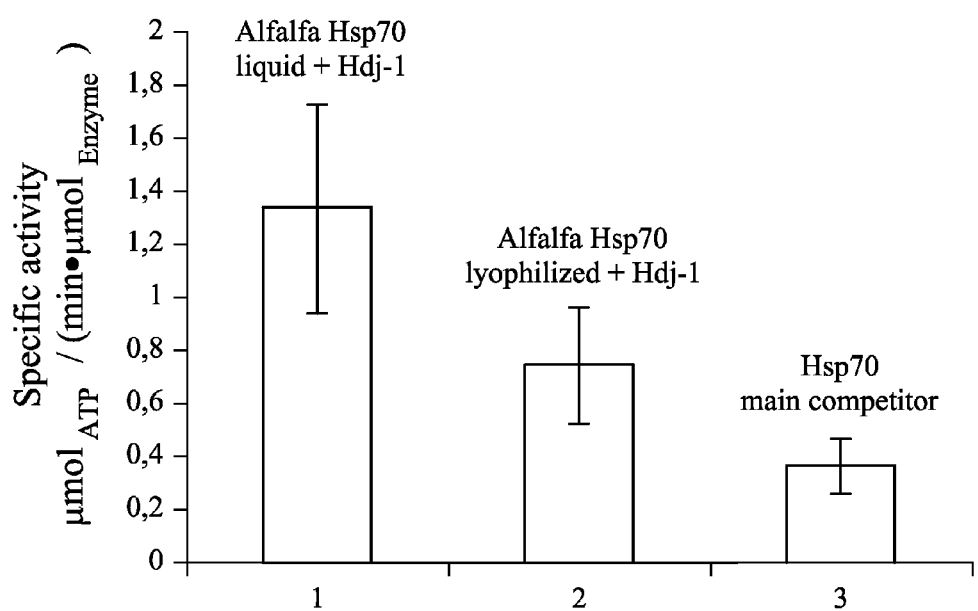

The isolated HSP70 showed a high ATPase activity which was 3 fold higher than the activity from the competitive product (Sigma Aldrich), see FIG. 2. ATPase assay was an ATPase-Aktivitity test with ATP-regenerating system and was based on the PhD-Thesis by Klaus Richter (2003) "Die ATP-Hydrolyse des molekularen Chaperons Hsp90 and ihre Regulation durch Co-Chaperone."

The HSP 70 yield was approximately 15 mg of pure Hsp70 out of 250 kg of fresh alfalfa (=0.06 mg/kg).

The invention claimed is:

1. A method for recovering a stress protein selected from the group consisting of HSP40, HSP60, HSP70 and HSP90 from a plant, comprising
   obtaining a liquid comprising the stress protein from the plant;
   precipitating one or more components other than the stress protein from the liquid;
   adding a fibrous filter aid and a mineral powder to the liquid; then
   subjecting the liquid comprising the stress protein, precipitated component(s), the fibrous filter aid and the mineral powder to a first filtration step over a filter, thereby separating the precipitate, fibrous filter aid and mineral powder from the filtrate comprising the stress protein; thereafter
   subjecting the filtrate to a further filtration step; and thereafter
   purifying the stress protein.

2. The method according to claim 1, wherein in the first filtration step chlorophyll and/or rubisco are removed from the liquid.

3. The method according to claim 1 wherein the mineral powder comprises at least one granular mineral.

4. The method according to claim 3, comprising at least one granular mineral selected from the group of diatomaceous earth and perlite.

5. The method according to claim 1, wherein the fibrous filter aid comprises cellulose fibres.

6. The method according to claim 1, wherein the fibrous filter aid is a mixture of fibres having a different length, the mixture at least providing fibres with a length over the range of about 20 μm to about 130 μum.

7. The method according to claim 1, wherein the further filtration step to which the filtrate is subjected is a depth filtration step.

8. The method according to claim 1, wherein after the further filtration step, a fraction comprising stress protein is subjected to a fluid removal step thereby concentrating the stress protein in the fraction and/or to a salt removal step.

9. The method according to claim 1 wherein the stress protein is purified by chromatography.

10. The method according to claim 9, wherein the chromatography comprises a first strong anion exchange step, thereafter an affinity chromatography separation step, and thereafter a second strong anion exchange step.

11. The method according to claim 10, wherein the median particle size of the exchange material used in the first anion exchange is larger than the median particle size of the exchange material used in the second anion exchange.

12. The method according to claim 1, wherein the stress protein is a stress protein from a plant selected from the group of Fabaceae, Chenopodiaceae, Solanaceae and Poaceae.

13. The method according to claim 1, wherein the filtrate of the first filtration step is subjected said further filtration step without first having been subjected to centrifugation.

14. The method according to claim 8, wherein the fluid removal step is reverse osmosis, ultrafiltration or nanofiltration, and the salt removal step is dialysis.

15. The method according to claim 1 wherein the stress protein is a stress protein from a plant selected from the group consisting of alfalfa, wheat, maize, rice, soy, potato, and beet.

* * * * *